(12) United States Patent
Kikuchi

(10) Patent No.: US 9,741,113 B2
(45) Date of Patent: Aug. 22, 2017

(54) IMAGE PROCESSING DEVICE, IMAGING DEVICE, IMAGE PROCESSING METHOD, AND COMPUTER-READABLE RECORDING MEDIUM

(71) Applicant: OLYMPUS CORPORATION, Shibuya-ku, Tokyo (JP)

(72) Inventor: Sunao Kikuchi, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 85 days.

(21) Appl. No.: 14/977,213

(22) Filed: Dec. 21, 2015

(65) Prior Publication Data

US 2016/0300342 A1 Oct. 13, 2016

Related U.S. Application Data

(63) Continuation of application No. PCT/JP2015/061005, filed on Apr. 8, 2015.

(51) Int. Cl.
*G06T 7/00* (2017.01)
*G06K 9/00* (2006.01)
(Continued)

(52) U.S. Cl.
CPC ........ *G06T 7/0012* (2013.01); *G06K 9/00228* (2013.01); *G06K 9/40* (2013.01);
(Continued)

(58) Field of Classification Search
CPC combination set(s) only.
See application file for complete search history.

(56) References Cited

U.S. PATENT DOCUMENTS

| 8,717,456 B2 * | 5/2014 | Johnson | H04N 5/217 348/222.1 |
| 8,730,601 B2 * | 5/2014 | Jess | G01J 3/0235 359/385 |

(Continued)

FOREIGN PATENT DOCUMENTS

| JP | 01280442 A | 11/1989 |
| JP | 09262213 A | 10/1997 |

(Continued)

OTHER PUBLICATIONS

Daniel McDuff, et al., "Improvements in Remote Cardio-Pulmonary Measurement Using a Five Band Digital Camera", 2014, IEEE Transactions on Biomedical Engineering, 8 Pages.

(Continued)

*Primary Examiner* — Anand Bhatnagar
(74) *Attorney, Agent, or Firm* — Holtz, Holtz & Volek PC

(57) ABSTRACT

An image processing device includes: an acquisition unit configured to acquire image data generated by an imaging element where each of narrow band filters constituting a predetermined array pattern is disposed at a position corresponding to any one of a plurality of pixels; a determination unit configured to determine whether or not a light amount of the invisible light range under an environment at the time when the imaging element generates the image data is larger than a threshold value; and a generation unit configured to generate vital information of a subject based on the determination result of the determination unit.

13 Claims, 13 Drawing Sheets

(51) Int. Cl.
*G06K 9/40* (2006.01)
*G06K 9/46* (2006.01)
*G02B 5/20* (2006.01)

(52) U.S. Cl.
CPC ............ *G06K 9/4652* (2013.01); *G02B 5/201* (2013.01); *G02B 5/208* (2013.01); *G06T 2207/30004* (2013.01)

(56) References Cited

U.S. PATENT DOCUMENTS

| | | | | |
|---|---|---|---|---|
| 9,215,984 | B2* | 12/2015 | Hattery | A61B 5/0059 |
| 9,282,305 | B2* | 3/2016 | Kikuchi | H04N 9/07 |
| 2005/0273011 | A1* | 12/2005 | Hattery | A61B 5/0059 |
| | | | | 600/476 |
| 2012/0013779 | A1* | 1/2012 | Hattery | A61B 5/0059 |
| | | | | 348/302 |
| 2012/0113287 | A1* | 5/2012 | Johnson | H04N 5/217 |
| | | | | 348/222.1 |
| 2013/0039553 | A1* | 2/2013 | Kjolby | A61B 5/026 |
| | | | | 382/128 |
| 2014/0092288 | A1* | 4/2014 | Hattery | A61B 5/0059 |
| | | | | 348/302 |
| 2014/0211306 | A1* | 7/2014 | Jess | G01J 3/0235 |
| | | | | 359/385 |
| 2015/0116555 | A1* | 4/2015 | Hayashi | H04N 9/045 |
| | | | | 348/280 |
| 2016/0252396 | A1* | 9/2016 | Tack | G01J 3/26 |

FOREIGN PATENT DOCUMENTS

| | | |
|---|---|---|
| JP | 2011143154 A | 7/2011 |
| JP | 2013118978 A | 6/2013 |

OTHER PUBLICATIONS

International Search Report (ISR) dated Jun. 23, 2015 issued in International Application No. PCT/JP2015/061005.

Lingqin Kong, et al., "Non-contact detection of oxygen saturation based on visible light imaging device using ambient light", Optics Express, vol. 21, No. 15, Jul. 29, 2013, pp. 17464-17471.

* cited by examiner

| C4 | C1 | C3 | C1 | C3 | C1 | C3 |
|----|----|----|----|----|----|----|
| C1 | C2 | C1 | C5 | C1 | C2 | C1 |
| C3 | C1 | C3 | C1 | C3 | C1 | C6 |
| C1 | C2 | C1 | C2 | C1 | C2 | C1 |
| C3 | C1 | C5 | C1 | C3 | C1 | C3 |
| C1 | C2 | C1 | C2 | C1 | C6 | C1 |
| C3 | C1 | C3 | C1 | C3 | C1 | C3 |

221

221a

| C4 | C5 | C4 | C5 | C4 | C5 | C4 |
|----|----|----|----|----|----|----|
| C5 | C6 | C5 | C6 | C5 | C6 | C5 |
| C4 | C5 | C4 | C5 | C4 | C5 | C4 |
| C5 | C6 | C5 | C6 | C5 | C6 | C5 |
| C4 | C5 | C4 | C5 | C4 | C5 | C4 |
| C5 | C6 | C5 | C6 | C5 | C6 | C5 |
| C4 | C5 | C4 | C5 | C4 | C5 | C4 |

IMAGE PROCESSING DEVICE, IMAGING DEVICE, IMAGE PROCESSING METHOD, AND COMPUTER-READABLE RECORDING MEDIUM

CROSS REFERENCES TO RELATED APPLICATIONS

This application is a continuation of PCT international application Ser. No. PCT/JP2015/061005 filed on Apr. 8, 2015 which designates the United States, incorporated herein by reference.

BACKGROUND

1. Technical Field

The disclosure relates to an image processing device, an imaging device, an image processing method, and a computer-readable recording medium, which generate vital information on a living body or the like based on image data.

2. Related Art

In the related art, in a medical field or a health field, a health state of a subject is checked by using vital information such as a heart rate, a degree of oxygen saturation, and a blood pressure as information for checking a health state of a person. For example, there is known a technique of irradiating a living body with red light and infrared light and performing imaging by using an image sensor, and calculating a degree of oxygen saturation of the living body based on image data generated by the image sensor (refer to Japanese Patent Application Laid-open No. 2013-118978). According to the technique, the degree of oxygen saturation of the living body is calculated based on a degree of light absorption of the living body calculated according to the image data generated by the image sensor and a time change in the degree of light absorption.

In addition, there is known a technique of irradiating a face area of a subject with red light and infrared light and generating vital information of the subject from a time change of moving image data imaged from the face of the subject in order to reduce a load to the subject (refer to Japanese Patent Application Laid-open No. 9-262213).

SUMMARY

In some embodiments, an image processing device includes: an acquisition unit configured to acquire image data generated by an imaging element where each of narrow band filters constituting a predetermined array pattern is disposed at a position corresponding to any one of a plurality of pixels, the narrow band filters being a first narrow band filter having a wavelength band narrower than a primary-color wavelength band and transmitting narrow band light having a maximum value of transmission spectrum in a visible light range, a second narrow band filter having a wavelength band narrower than the primary-color wavelength band and transmitting narrow band light having a maximum value of transmission spectrum in a visible light range different from that of the first narrow band filter, and a third narrow band filter transmitting narrow band light having a maximum value of transmission spectrum in an invisible light range; a determination unit configured to determine whether or not a light amount of the invisible light range under an environment at the time when the imaging element generates the image data is larger than a threshold value; and a generation unit configured to generate vital information of a subject by using a pixel value corresponding to the position of the pixel where the third narrow band filter is disposed and a pixel value corresponding to the position of the pixel where the second narrow band filter is disposed in an image corresponding to the image data in a case where the determination unit determines that the light amount of the invisible light range is larger than the threshold value and to generate vital information of a subject by using a pixel value corresponding to the position of the pixel where the first narrow band filter is disposed and a pixel value corresponding to the position of the pixel where the second narrow band filter is disposed in the image corresponding to the image data in a case where the determination unit determines that the light amount of the invisible light range is equal to or smaller than the threshold value.

In some embodiments, an imaging device includes: the image processing device; and the imaging element.

In some embodiments, an image processing method executed by an image processing device includes: an acquisition step of acquiring image data generated by an imaging element where each of narrow band filters constituting a predetermined array pattern is disposed at a position corresponding to any one of a plurality of pixels, the narrow band filters being a first narrow band filter having a wavelength band narrower than a primary-color wavelength band and transmitting narrow band light having a maximum value of transmission spectrum in a visible light range, a second narrow band filter having a wavelength band narrower than the primary-color wavelength band and transmitting narrow band light having a maximum value of transmission spectrum in a visible light range different from that of the first narrow band filter, and a third narrow band filter transmitting narrow band light having a maximum value of transmission spectrum in an invisible light range; a determination step of determining whether or not a light amount of the invisible light range under an environment at the time when the imaging element generates the image data is larger than a threshold value; and a generation step of generating vital information of a subject by using a pixel value corresponding to the position of the pixel where the third narrow band filter is disposed and a pixel value corresponding to the position of the pixel where the second narrow band filter is disposed in an image corresponding to the image data in a case where it is determined in the determination step that the light amount of the invisible light range is larger than the threshold value and generating the vital information of the subject by using a pixel value corresponding to the position of the pixel where the first narrow band filter is disposed and a pixel value corresponding to the position of the pixel where the second narrow band filter is disposed in the image corresponding to the image data in a case where it is determined in the determination step that the light amount of the invisible light range is equal to or smaller than the threshold value.

In some embodiments, a non-transitory computer-readable recording medium recording a program for causing an image processing device to execute: an acquisition step of acquiring image data generated by an imaging element where each of narrow band filters constituting a predetermined array pattern is disposed at a position corresponding to any one of a plurality of pixels, the narrow band filters being a first narrow band filter having a wavelength band narrower than a primary-color wavelength band and transmitting narrow band light having a maximum value of transmission spectrum in a visible light range, a second narrow band filter having a wavelength band narrower than the primary-color wavelength band and transmitting narrow band light having a maximum value of transmission spectrum in a visible light range different from that of the first narrow band filter, and a third narrow band filter transmitting narrow band light having a maximum value of transmission spectrum in an invisible light range; a determination step of determining whether or not a light amount of the invisible light range under an environment at the time when the imaging element generates the image data is larger than a threshold value; and a generation step of generating vital information of a subject by using a pixel value corresponding to the position of the pixel where the third narrow band filter is disposed and a pixel value corresponding to the position of the pixel where the second narrow band filter is disposed in an image corresponding to the image data in a case where it is determined in the determination step that the light amount of the invisible light range is larger than the threshold value and generating the vital information of the subject by using a pixel value corresponding to the position of the pixel where the first narrow band filter is disposed and a pixel value corresponding to the position of the pixel where the second narrow band filter is disposed in the image corresponding to the image data in a case where it is determined in the determination step that the light amount of the invisible light range is equal to or smaller than the threshold value.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, embodiments for embodying the present invention will be described in detail with reference to the drawings. In addition, the present invention is not limited by the following embodiments. In addition, each figure referred to in the description hereinafter schematically illustrates shapes, sizes, and positional relations to such an extent that the contents of the present invention can be understood. Namely, the present invention is not limited only to the shapes, sizes, and positional relations exemplified in each figure. In addition, in the description, the same components are denoted by the same reference signs.

First Embodiment

Configuration of Imaging Device

Figure 1:
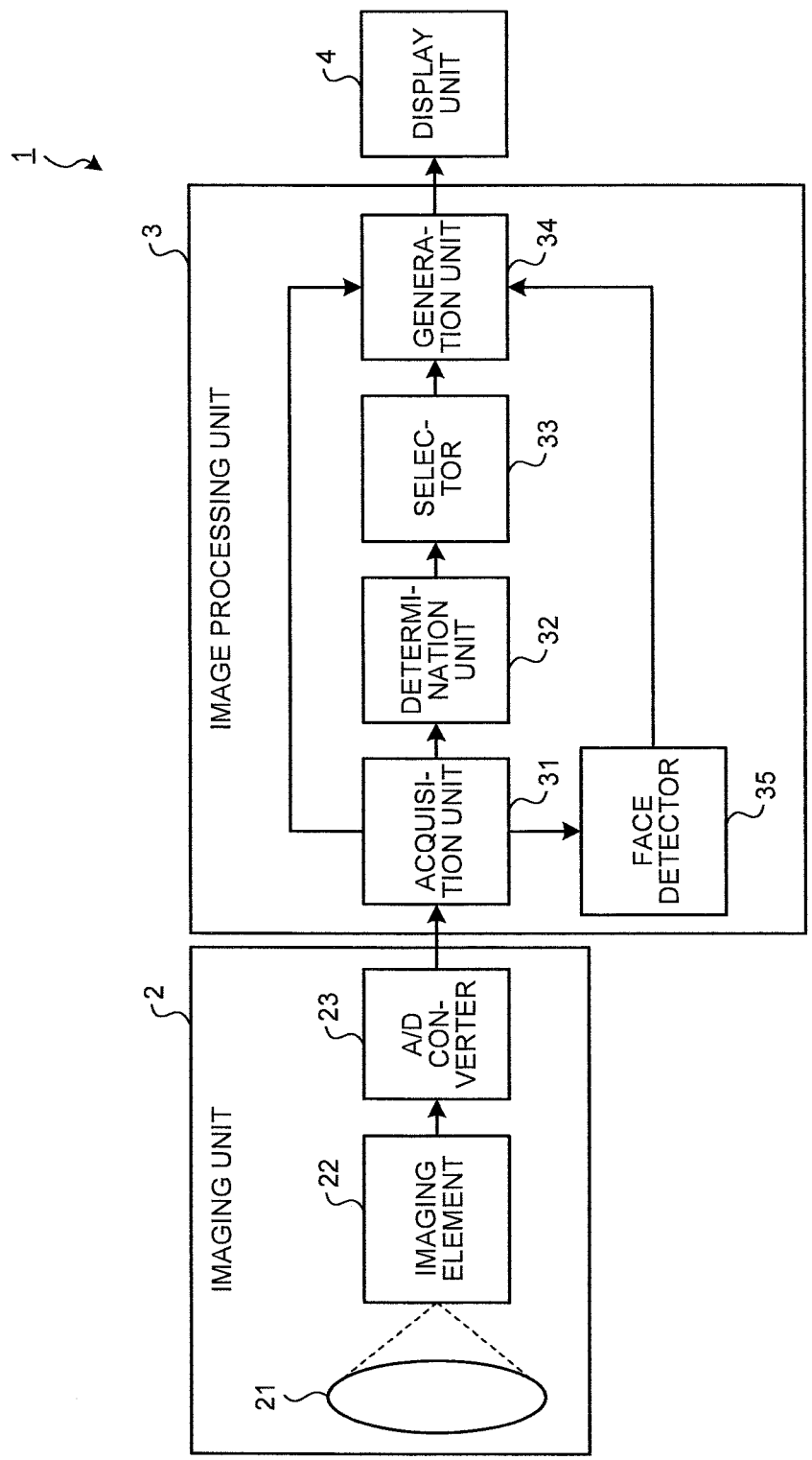
FIG. 1 is a block diagram illustrating a schematic configuration of an imaging device according to a first embodiment of the present invention.

FIG. 1 is a block diagram illustrating a schematic configuration of an imaging device according to a first embodiment of the present invention. An imaging device 1 illustrated in FIG. 1 is configured to include an imaging unit 2 which images a subject to generate RAW image data of the subject, an image processing unit 3 which acquires the RAW image data generated by the imaging unit 2 and performs a predetermined process on the acquired RAW image data, and a display unit 4 which displays an image corresponding to the RAW image data on which the image processing unit 3 performs the process. In addition, in the first embodiment, the image processing unit 3 functions as an image processing device. In addition, in the first embodiment, the imaging unit 2, the image processing unit 3, and the display unit 4 are connected to each other so as to be bi-directionally communicatable in a wire or wireless manner.

Configuration of Imaging Unit

First, a configuration of the imaging unit 2 will be described.

The imaging unit 2 is configured to include an optical system 21, an imaging element 22, and an A/D converter 23.

The optical system 21 configured with one or a plurality of lenses, for example, a focus lens or a zoom lens, a diaphragm, a shutter, and the like to form a subject image on a light-receiving plane of the imaging element 22.

The imaging element 22 receives the subject image formed on the light-receiving plane by the optical system 21 and performs photo-electric conversion to generate RAW image data. The imaging element 22 is configured with a CMOS (complementary metal oxide semiconductor) which photo-electrically converts light received by a plurality of pixels arrayed in a grid pattern to generate an electrical signal. In addition, the imaging element 22 is configured with a filter array (CFA) including a plurality of wide band filters which transmit light of primary-color wavelength bands and a plurality of narrow band filters which transmit light of narrow bands which are narrower than the wavelength bands of the light transmitted by the wide band filters.

Figures 2, 3:
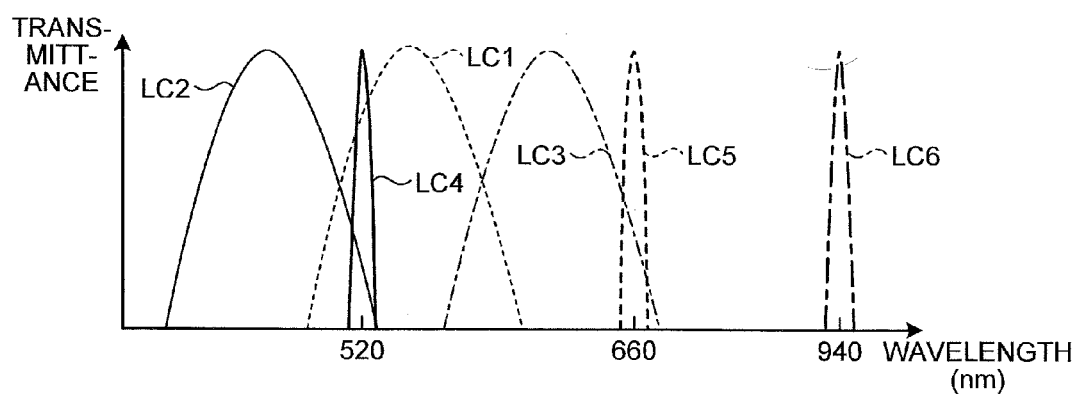
FIG. 2 is a schematic diagram illustrating a configuration of a filter array installed in an imaging element according to the first embodiment of the present invention.
FIG. 3 is a diagram illustrating an example of spectral sensitivity characteristics of filters constituting the filter array installed in the imaging element according to the first embodiment of the present invention.

FIG. 2 is a schematic diagram illustrating a configuration of the filter array. A filter array 221 illustrated in FIG. 2 is configured by disposing, on light-receiving planes of respective pixels constituting the imaging element 22, wide band filters C1 transmitting green light (495 to 570 nm), wide band filters C2 transmitting blue light (450 to 495 nm), wide band filters C3 transmitting red light (620 to 750 nm), narrow band filters C4 (first narrow band filters) transmitting light component which has a maximum value in a portion of a green wavelength band and is narrower than the green wavelength band, narrow band filters C5 (second narrow band filters) transmitting light component which has a maximum value in a portion of a red wavelength band and is narrower than the red wavelength band, and narrow band filters C6 (third narrow band filters) transmitting infrared light component. In the filter array 221, a sum of the wide band filters C1, the wide band filters C2, and the wide band filters C3 is larger than a sum of the narrow band filters C4, the narrow band filters C5, and the narrow band filters C6. More specifically, in the filter array 221, as seen from one narrow band filter as a reference, the narrow band filter is disposed at a position where goes rightward by three pixels and goes downward by one pixel. More specifically, in the filter array 221, as seen from the narrow band filter C4 at the upper-left corner of FIG. 2 as a reference, the narrow band filter C5 is disposed at the position which goes rightward in the order of the wide band filter C1, the wide band filter C3, and the wide band filter C1 and goes downward by one pixel.

FIG. 3 is a diagram illustrating an example of spectral sensitivity characteristics of the filters constituting the filter array 221. In addition, in FIG. 3, the horizontal axis denotes wavelength, and the vertical axis denotes transmittance. In FIG. 3, a curve LC1 shows transmittance of the wide band filters C1, a curve LC2 shows transmittance of the wide band filters C2, a curve LC3 shows transmittance of the wide band filters C3, a curve LC4 shows transmittance of the narrow band filters C4, a curve LC5 shows transmittance of the narrow band filters C5, and a curve LC6 shows transmittance of the narrow band filters C6.

As illustrated in FIG. 3, the narrow band filters C4 transmits narrow band light included in a portion of the green wavelength band. More specifically, the narrow band filters C4 transmits narrow band light included in a wavelength band of 490 to 550 nm. More preferably, the narrow band filters C4 transmits light of 520 nm. In addition, the narrow band filters C5 transmits narrow band light included in a portion of the red wavelength band. More specifically, the narrow band filters C5 transmits narrow band light included in a wavelength band of 620 to 700 nm. More preferably, the narrow band filters C5 transmits light of 660 nm. In addition, the narrow band filters C6 transmits narrow band light included in a portion of the near-infrared wavelength band. More specifically, the narrow band filters C6 transmits narrow band light included in a wavelength band of 800 to 1000 nm. More preferably, the narrow band filters C6 transmits light of 940 nm. In addition, in the first embodiment, a transmission spectrum transmitted by the narrow band filters C4, a transmission spectrum transmitted by the narrow band filters C5, and a transmission spectrum transmitted by the narrow band filters C6 are described to be 520 nm, 660 nm, and 940 nm, respectively.

Returning to FIG. 1, the description of the configuration of the imaging unit 2 is resumed.

The A/D converter 23 converts the analog RAW image data generated by the imaging element 22 to digital RAW image data.

Configuration of Image Processing Unit

Next, a configuration of the image processing unit 3 will be described.

The image processing unit 3 is configured to include an acquisition unit 31, a determination unit 32, a selector 33, a generation unit 34, and a face detector 35.

The acquisition unit 31 acquires the RAW image data generated by the imaging element 22 from the imaging unit 2 and outputs the acquired RAW image data to the determination unit 32, the generation unit 34, and the face detector 35.

The determination unit 32 determines whether or not a light amount in the invisible light range under the environment when the imaging element 22 generates the image data is larger than a threshold value. More specifically, the determination unit 32 determines whether or not near-infrared information is included in the RAW image data acquired by the acquisition unit 31 from the imaging unit 2. For example, the determination unit 32 determines whether or not the light amount (near-infrared information) in the invisible light range under the environment when the imaging element 22 generates the image data is larger than the threshold value by extracting pixel values of the pixels corresponding to the positions of the pixels where the narrow band filters C6 are disposed in the image corresponding to the RAW image data acquired by the acquisition unit 31 from the imaging unit 2, calculating an average value of the extracted pixel values of the pixels corresponding to the narrow band filters C6, and determining whether or not the calculated average value is larger than the threshold value.

The selector 33 selects the narrow band filters which the generation unit 34 is to use to generate the vital information based on the determination result of the determination unit 32. More specifically, in a case where the determination unit 32 determines that sufficient near-infrared information is included in the RAW image data, the selector 33 selects the narrow band filters C6 as the narrow band filters (bands) which the generation unit 34 is to use to generate the vital information; and in a case where the determination unit 32 determines that sufficient near-infrared information is not included in the RAW image data, the selector selects the narrow band filters C4 as the narrow band filters which the generation unit 34 is to use to generate the vital information.

The generation unit 34 generates vital information of a face area including a face of a subject included in the RAW image corresponding to the RAW image data based on the selection result of the selector 33, the RAW image data acquired by the acquisition unit 31 from the imaging unit 2 and the detection result of the face detector 35. Herein, the vital information is any one of a degree of oxygen saturation, a heart rate, and a blood pressure. More specifically, in a case where the determination unit 32 determines that the light amount of the invisible light range is larger than the threshold value, the generation unit 34 generates the vital information of the subject by using the pixel values corresponding to the positions of the pixels where the narrow band filters C4 are disposed and the pixel values corresponding to the positions of the pixels where the narrow band filters C5 are disposed in the image corresponding to the RAW image data generated by the imaging element 22; and in a case where the determination unit 32 determines that the light amount of the invisible light range is equal to or smaller than the threshold value, the generation unit generates the vital information of the subject by using the pixel values corresponding to the positions of the pixels where the narrow band filters C4 are disposed and the pixel values corresponding to the positions of the pixels where the narrow band filters C5 are disposed in the image corresponding to the image data generated by the imaging element 22.

The face detector 35 detects an area including the face of the subject included in the image corresponding to the RAW image data input from the acquisition unit 31 by using well-known pattern matching or the like and outputs the detection result to the generation unit 34.

Configuration of Display Unit

Next, a configuration of the display unit 4 will be described.

The display unit 4 displays the image corresponding to the image data which are processed by the image processing unit 3. The display unit 4 is configured by using a display panel such as an organic EL (electroluminescence) device or a liquid crystal device or a display driver or the like.

The imaging device 1 having the above configuration images the subject by using the imaging unit 2 to generate the RAW image data of the subject. The image processing unit 3 generates the vital information of the subject by using the RAW image data generated by the imaging unit 2. The display unit 4 displays the vital information of the subject generated by the image processing unit 3. Therefore, a user can intuitively recognize the vital information.

Processes of Image Processing Unit

Figure 4:
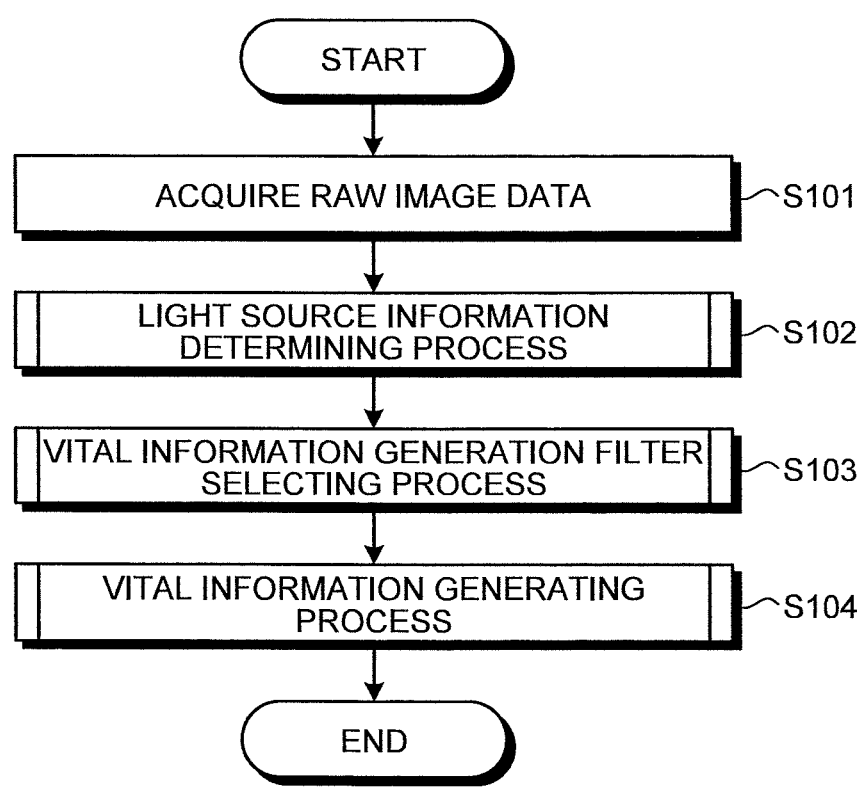
FIG. 4 is a flowchart illustrating a summary of processes executed by an image processing unit according to the first embodiment of the present invention.

Next, processes executed by the image processing unit 3 will be described. FIG. 4 is a flowchart illustrating a summary of the processes executed by the image processing unit 3.

As illustrated in FIG. 4, first, the acquisition unit 31 acquires the RAW image data from the imaging unit 2 (step S101).

Subsequently, the determination unit 32 executes a light source information determining process of determining whether or not sufficient near-infrared information is included based on the RAW image data acquired by the acquisition unit 31 from the imaging unit 2 (step S102).

Summary of Light Source Information Determining Process

Figure 5:
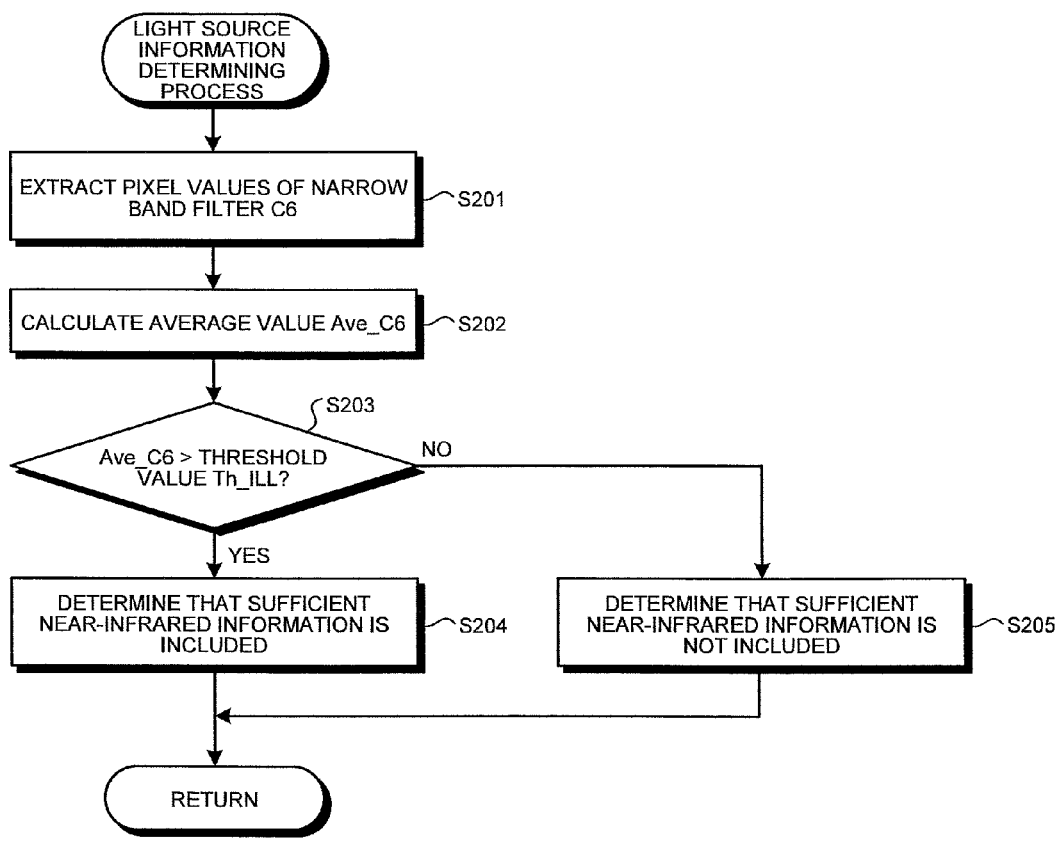
FIG. 5 is a flowchart illustrating a summary of a light source information determining process of FIG. 4.

FIG. 5 is a flowchart illustrating a summary of the light source information determining process of the above-described step S102.

As illustrated in FIG. 5, the determination unit 32 extracts the pixel values of the pixels corresponding to the narrow band filters C6 from the RAW image data acquired by the acquisition unit 31 from the imaging unit 2 (step S201), and the determination unit 32 calculates the average value Ave_C6 over the entire image corresponding to the RAW image data (step S202). Herein, the average value Ave_C6 is a value obtained by adding the pixel values of the pixels corresponding to the narrow band filters C6 from the RAW image data and performing averaging.

Next, the determination unit 32 determines whether or not the average value Ave_C6 calculated in step S202 is larger than the threshold value Th_ILL (step S203). Herein, the threshold value Th_ILL is a value calculated from an experiment or the like in advance. In a case where the average value Ave_C6 is larger than the threshold value Th_ILL (step S203: Yes), the determination unit 32 determines that sufficient near-infrared information is included in the RAW image data (step S204). After step S204, the image processing unit 3 returns to a main routine of FIG. 4.

In a case where the average value Ave_C6 is equal to or smaller than the threshold value Th_ILL in step S203 (step S203: No), the determination unit 32 determines that sufficient near-infrared information is not included in the RAW image data (step S205). After step S205, the image processing unit 3 returns to the main routine of FIG. 4.

Returning to FIG. 4, the steps following step S103 continue to be described.

In step S103, the selector 33 executes a vital information generation filter selecting process for select a filter for generating the vital information based on the determination result of the determination unit 32.

Summary of Vital Information Generation Filter Selecting Process

Figure 6:
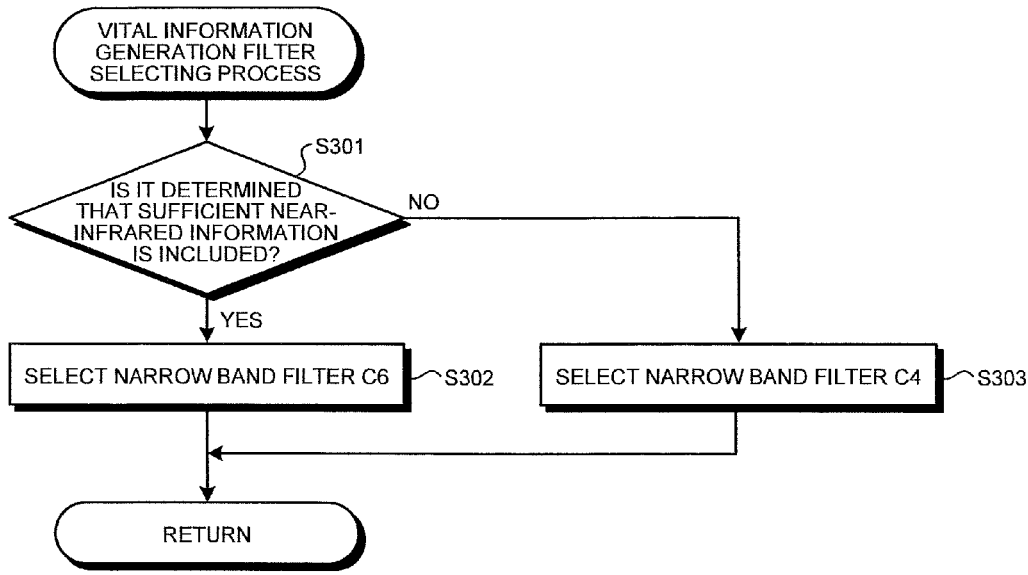
FIG. 6 is a flowchart illustrating a summary of a vital information generation filter selecting process of FIG. 4.

FIG. 6 is a flowchart illustrating a summary of the vital information generation filter selecting process of the above-described step S103.

As illustrated in FIG. 6, in a case where the determination unit 32 determines that sufficient near-infrared information is included in the RAW image data (step S301: Yes), the selector 33 selects the narrow band filters C6 as the narrow band filters which the generation unit 34 is to use to generate the vital information (step S302). After step S302, the image processing unit 3 returns to the main routine of FIG. 4.

In a case where the determination unit 32 determines in step S301 that sufficient near-infrared information is not included in the RAW image data (step S301: No), the selector 33 selects the narrow band filters C4 as the narrow band filters which the generation unit 34 is to use to generate the vital information (step S303). After step S303, the image processing unit 3 returns to the main routine of FIG. 4.

Figure 7:
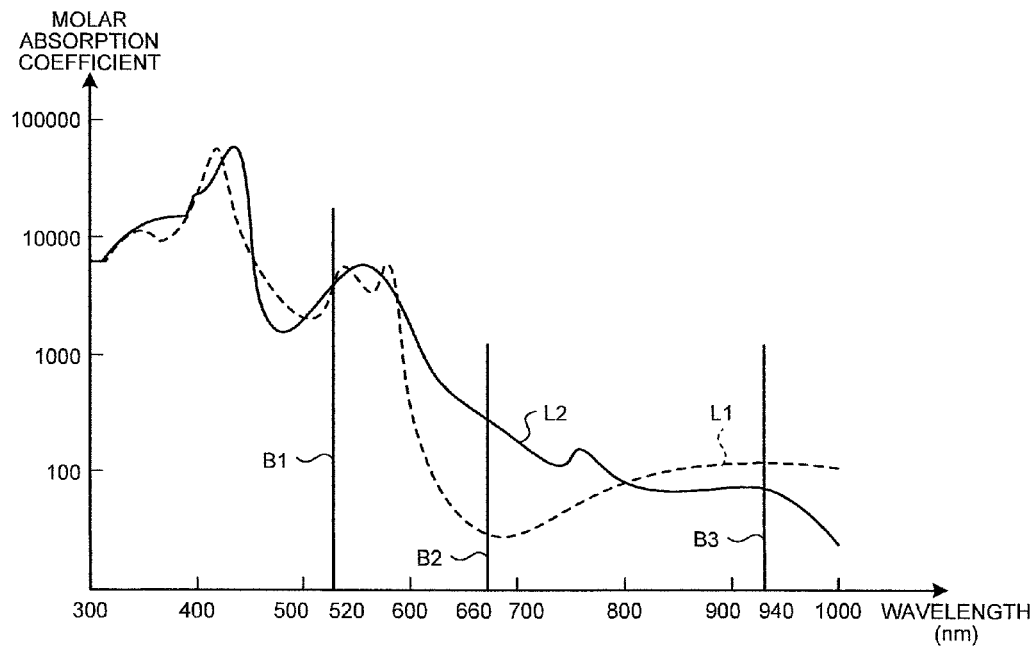
FIG. 7 is a diagram illustrating hemoglobin absorption characteristics.

Now, the wavelength band of the filter used for generating the vital information will be described in detail. FIG. 7 is a diagram illustrating hemoglobin absorption characteristics. In FIG. 7, the horizontal axis represents wavelength (nm), and the vertical axis represents a molar absorption coefficient (cm$^{-1}$/m). In addition, in FIG. 7, a curve L1 represents the molar absorption coefficient of reduced hemoglobin, and a curve L2 represents the molar absorption coefficient of oxygenated hemoglobin. In addition, in FIG. 7, a straight line B1 represents a wavelength band corresponding to the narrow band filter C4, a straight line B2 represents a wavelength band corresponding to the narrow band filter C5, and a straight line B3 represents a wavelength band corresponding to the narrow band filter C6.

In the types of hemoglobin in blood, there are two types of reduced hemoglobin (Hb) which is not combined with oxygen and oxygenated hemoglobin (HbO$_2$) which is combined with oxygen. As one of the vital information used in the first embodiment, there is a degree of oxygen saturation (SPO$_2$) indicating a ratio of the oxygenated hemoglobin to the entire hemoglobin in blood. The degree of oxygen saturation is calculated by the following Equation (1).

$$SPO_2 = (C((HbO_2)/(C(HbO_2)+(C(Hb)))) \times 100 \qquad (1)$$

Herein, C((HbO$_2$) represents a concentration of the oxygenated hemoglobin, and C(Hb) represents a concentration of the reduced hemoglobin.

In the first embodiment, used is a difference in absorption characteristics of the oxygenated hemoglobin and the reduced hemoglobin for every wavelength. Namely, as illustrated in FIG. 7, in the first embodiment, the generation unit 34 calculates the degree of oxygen saturation as the vital information by using wavelength 660 nm where the difference in absorption characteristics of the oxygenated hemoglobin and the reduced hemoglobin is large and wavelength 940 nm or wavelength 520 nm where the difference in absorption characteristics of the oxygenated hemoglobin and the reduced hemoglobin is small (in addition, for the principle method for obtaining a degree of oxygen saturation, refer to Japanese Patent Application Laid-open No. 2013-118978, and in addition, for a method of estimating a degree of oxygen saturation in a non-contact manner (method of indirectly estimating by using image data), refer to Lingqin Kong et al., "Non-contact detection of oxygen saturation based on visible light imaging device using ambient light", Optics Express, Vol. 21, Issue 15, pp. 17464-17471 (2013)). Therefore, in a case where the determination unit 32 determines that sufficient near-infrared information is included in the RAW image data, the selector 33 selects the narrow band filter the narrow band filter C6 as the filter which the generation unit 34 is to use to generate the vital information; and in a case where the determination unit 32 determines that sufficient near-infrared information is not included in the RAW image data, the selector 33 selects the narrow band filter C4 as the filter which the generation unit 34 is to use to generate the vital information.

Returning to FIG. 4, the steps following step S104 continue to be described.

In step S104, the generation unit 34 executes a vital information generating process of generating vital information of a face area including a face of a subject included in the RAW image corresponding to the RAW image data based on the selection result of the selector 33 and the RAW image data acquired by the acquisition unit 31 from the imaging unit 2.

Summary of Vital Information Generating Process

Figure 8:
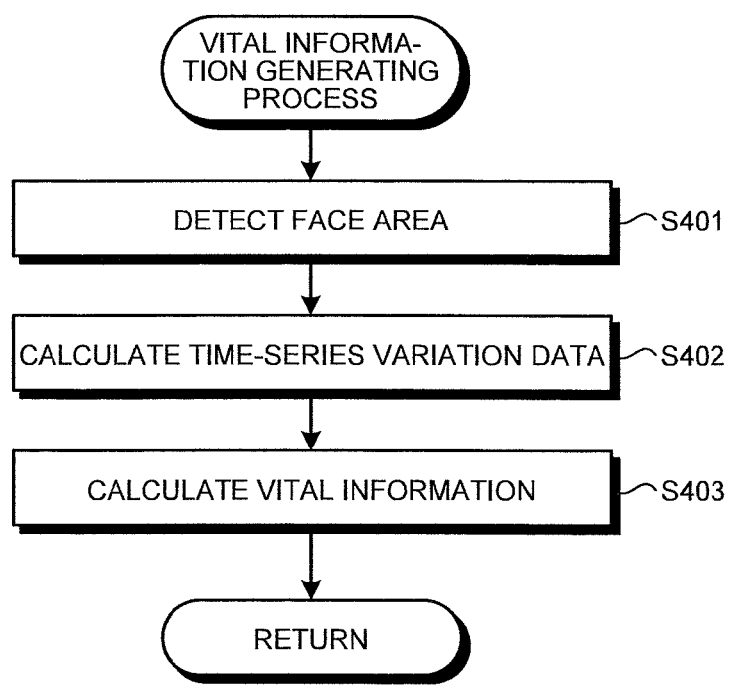
FIG. 8 is a flowchart illustrating a summary of a vital information generating process of FIG. 4.

FIG. 8 is a fluid injector a summary of the vital information generating process of the above-described step S104.

Figure 9:
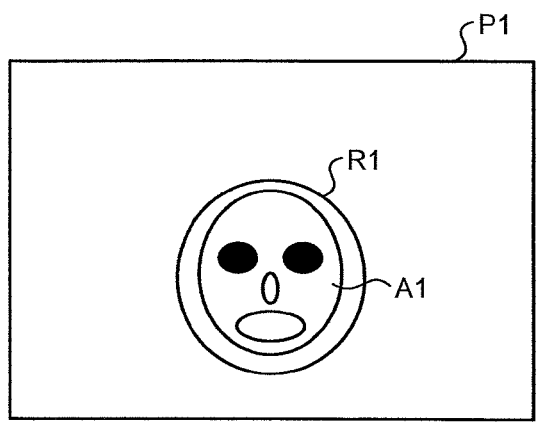
FIG. 9 is a diagram illustrating an example of an image corresponding to RAW image data generated by an imaging unit according to the first embodiment of the present invention.

As illustrated in FIG. 8, the face detector 35 detects a face area including a face of the subject included in the RAW image corresponding to the RAW image data acquired by the acquisition unit 31 from the imaging unit 2 (step S401). More specifically, as illustrated in FIG. 9, the face detector 35 detects a face area R1 including a face of a subject A1 in wide band image P1 (color image) corresponding to the image data of the pixel values of the wide band filters C1 to C3 included in the RAW image data by using a technique of well-known pattern matching or the like.

Subsequently, the generation unit 34 calculates time-series variation data for the ratio of the pixel value of the pixels corresponding to the narrow band filter selected by the selector 33 in the above-described step S103 and the pixel value of the pixel corresponding to the narrow band filter C5 (step S402).

Figures 10, 11:
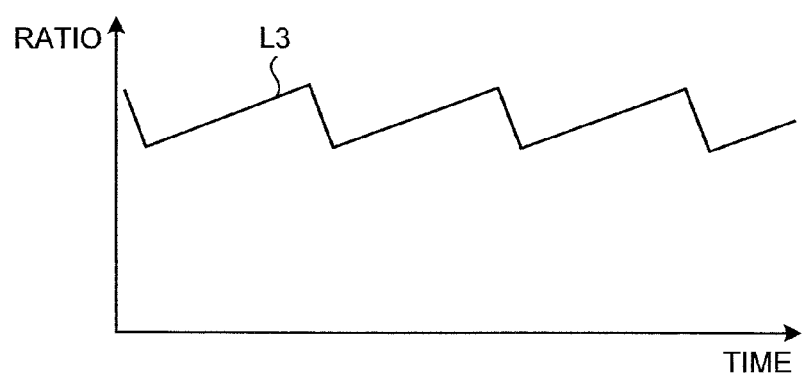
FIG. 10 is a schematic diagram illustrating time-series variation of a pixel value of a pixel corresponding to a narrow band filter selected by a selector of the image processing unit according to the first embodiment of the present invention.
FIG. 11 is a schematic diagram illustrating a configuration of a filter array installed in an imaging element according to a second embodiment of the present invention.

FIG. 10 is a schematic diagram illustrating the pixel value of the pixel corresponding to the narrow band filter selected by the selector 33 in the above-described step S103. For example, the figure is a schematic diagram illustrating time-series variation of the pixel value of the pixel corresponding to the narrow band filter C5. In FIG. 10, the horizontal axis represents the time, and the vertical axis represents the ratio. In addition, a sawtooth line L3 represents time-series variation of the pixel values added over the all the pixels corresponding to the narrow band filters C5 selected by the selector 33.

Herein, the reason why the generation unit 34 uses time-series variation data is that, although the generation unit 34 can calculate a degree of oxygen saturation by observing the above-described two wavelengths, particularly effective vital information is a degree of oxygen saturation of arterial blood. As the living body, there exist a tissue layer, an arterial layer, and a venous layer besides the blood. Among the tissue layers, a thickness of the arterial layer is changed in a short time, but a thickness of the tissue such as skin or flesh or the venous layer is not changed in a short time. Therefore, the generation unit 34 detects the component of only the arterial blood by detecting a varying component of time-series data about a ratio of a value (for example, refer to FIG. 10) obtained by adding the pixel values of the pixels corresponding to the narrow band filters selected by the selector 33 and a value obtained by adding the pixel values of the pixels corresponding to the narrow band filters C5. Namely, the generation unit 34 calculates the degree of oxygen saturation of the arterial blood based on the varying component of the time-series data of the ratio of the value obtained by adding the pixel values of the pixels corresponding to the narrow band filters selected by the selector 33 and the value obtained by adding the pixel values of the pixels corresponding to the narrow band filters C5.

In step S403, the generation unit 34 calculates the vital information based on the time-series variation data calculated in the above-described step S402. In addition, the vital information is not limited to the degree of oxygen saturation, but the generation unit 34 may generate a plurality of types of vital information including a heat rate calculated from the varying component of time-series data, emotion or stress (refer to McDuff, S. Gontarek, R. W. Picard, "Improvements in Remote Cardio-Pulmonary Measurement Using a Five Band Digital Camera", IEEE Transactions on Biomedical Engineering, (2014) obtained by calculating heart rates of a plurality of positions, calculating a pulse wave speed having high correlation to blood pressure from time difference thereof, and comparing with predetermined time-series data, or the like. In addition, the generation unit 34 output the vital information generated in step S403 to the display unit 4. Therefore, the user can intuitively recognize the vital information. After step S403, the image processing unit 3 returns to the main routine of FIG. 4, and the process is ended.

According to the first embodiment of the present invention described heretofore, in a case where the determination unit 32 determines that sufficient near-infrared information corresponding to the light amount of the invisible light range is included in the RAW image data, the generation unit 34 generates the vital information of the subject by the pixel values of the pixels where the narrow band filters C5 are disposed and the pixel values of the pixels where the narrow band filters C6 are disposed; and in a case where the determination unit 32 determines that sufficient near-infrared information corresponding to the light amount of the invisible light range is not included, the generation unit 34 generates the vital information of the subject by using the pixel values of the pixels where the narrow band filters C5 are disposed and the pixel values of the pixels where the narrow band filters C4 are disposed. Therefore, since a light source of emitting invisible light may not be installed, it is possible to miniaturize the device.

In addition, according to the first embodiment of the present invention, since the generation unit 34 generates the vital information of the subject based on the RAW image data generated by the imaging element 22, there is no need to accurately emit light of a specific wavelength band in outdoor measurement such as digital signage and a usage scene for an unspecified number of subjects as a target, so that it is possible to easily generate the vital information of the subject.

In addition, according to the first embodiment of the present invention, since the generation unit 34 generates the vital information of the subject based on the RAW image data generated by the imaging element 22 having the filter array 221 including the narrow band filters C6, in the case of acquiring the vital information in a non-contact manner, it is possible to acquire the vital information at a high accuracy without irradiation of the invisible light.

Furthermore, according to the first embodiment of the present invention, in a case where sufficient near-infrared information cannot be obtained under the environment at the time of measurement for the subject, for example, even in a case where measurement is performed under the environment of the light source such as a fluorescent light lamp which does not include sufficient near-infrared component, since the generation unit 34 generates the vital information of the subject by using the pixel values of the pixels corresponding to the narrow band filters C4, it is possible to acquire highly-accurate vital information.

In addition, according to the first embodiment of the present invention, even in a case where invisible light is not irradiated, the selector 33 selects appropriate narrow band filters according to the environment of the light source at the time of shooting, and the generation unit 34 generates the vital information by using the pixel values of the pixels corresponding to the narrow band filters selected by the selector 33, it is possible to acquire highly-accurate vital information.

In addition, in the first embodiment of the present invention, the face detector 35 may detect an expression (for example, a smiling face) of the face of the subject by using well-known techniques. In this case, the generation unit 34 may generate the vital information of the subject by using the expression of the face detected by the face detector 35 and the pixel values of the pixels where the narrow band filters selected by the selector 33 are disposed.

Second Embodiment

Next, a second embodiment of the present invention will be described. An imaging device according to the first embodiment is different from that of the above-described first embodiment in terms of the configuration of the imaging element 22. More specifically, in an imaging element according to the second embodiment, color filters are formed only in the narrow band filters. In addition, an imaging device according to the second embodiment is different in terms of the light source information determining process executed by the determination unit. Therefore, hereinafter, the configuration of the imaging element according to the second embodiment will be described, and after that, the light source information determining process executed by the determination unit according to the second embodiment will be described. In addition, hereinafter, the same components as those of the imaging device 1 according to the first embodiment are denoted by the same reference signs, and the description thereof is omitted.

Figure 12:
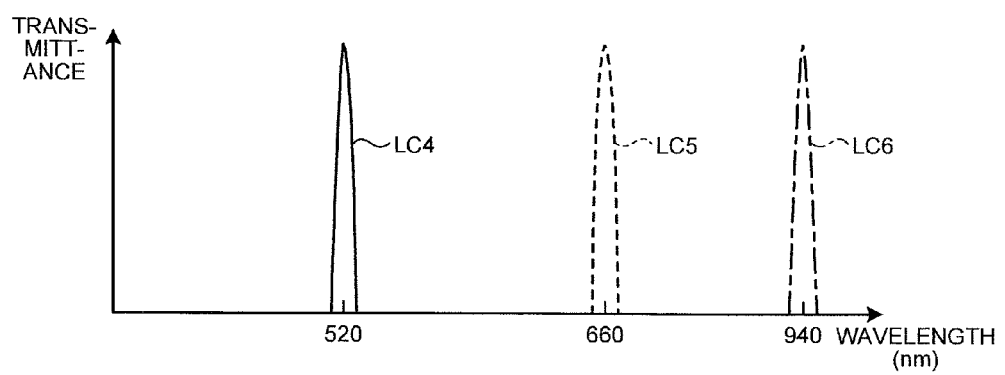
FIG. 12 is a diagram illustrating an example of spectral sensitivity characteristics of filters constituting the filter array installed in the imaging element according to the second embodiment of the present invention.

FIG. 11 is a schematic diagram illustrating a configuration of a filter array of the imaging element according to the second embodiment. FIG. 12 is a diagram illustrating an example of spectral sensitivity characteristics of the filters constituting the filter array. In addition, in FIG. 12, the horizontal axis represents wavelength, and the vertical axis represents transmittance.

As illustrated in FIGS. 11 and 12, a filter array 221a is disposed on the light-receiving planes of the pixels constituting the imaging element 22 and is configured by using the narrow band filters C4 to C6. In the filter array 221a, the number of narrow band filters C5 is larger than the number of narrow band filters C4 and the number of narrow band filters C6, and the number of narrow band filters C4 is equal to the number of narrow band filters C6.

Summary of Light Source Information Determining Process

Figure 13:
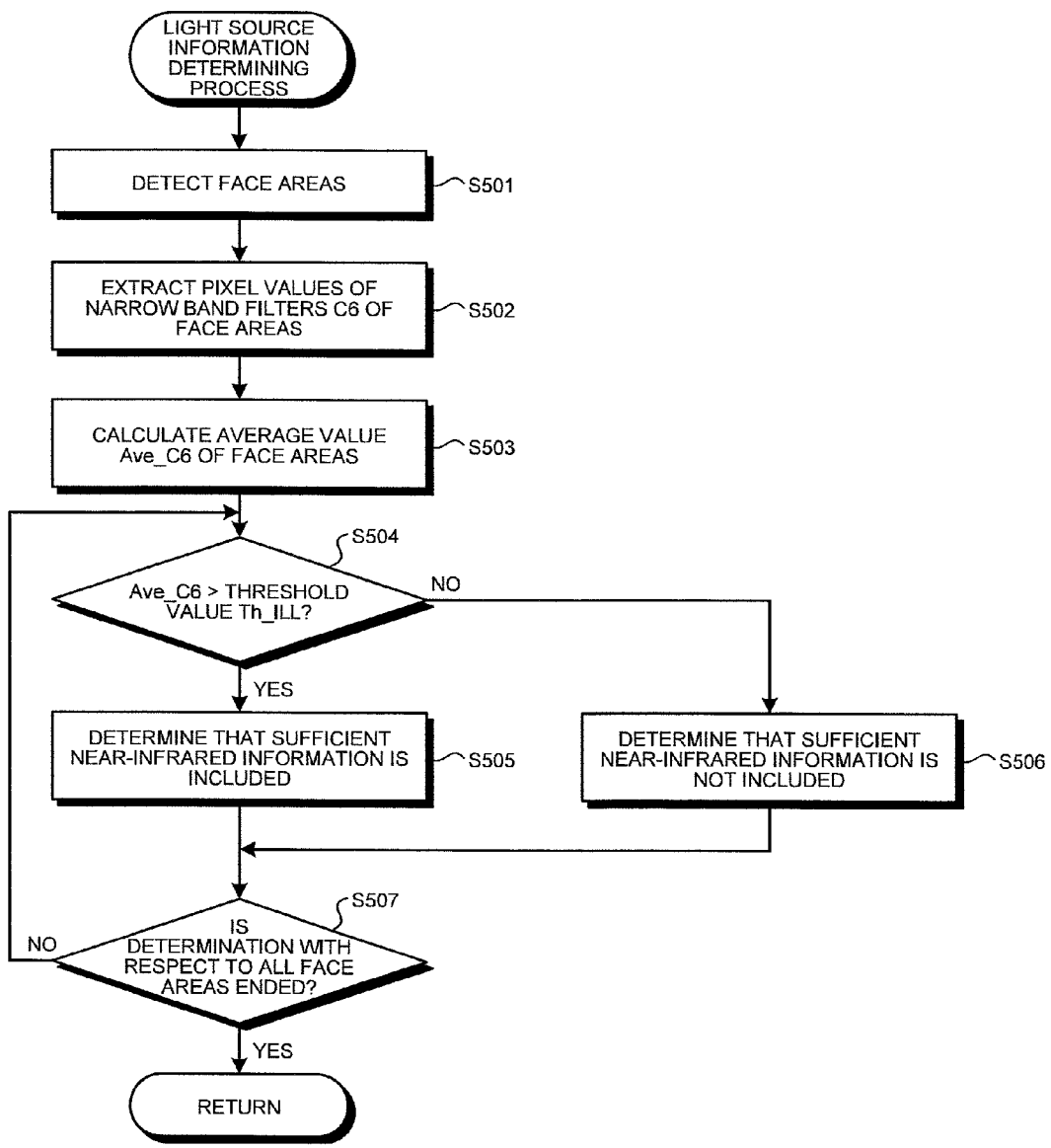
FIG. 13 is a flowchart illustrating a summary of a light source information determining process executed by an image processing unit according to the second embodiment of the present invention.

Now, the light source information determining process executed by the image processing unit 3 will be described. FIG. 13 is a flowchart illustrating a summary of the light source information determining process.

Figure 14:
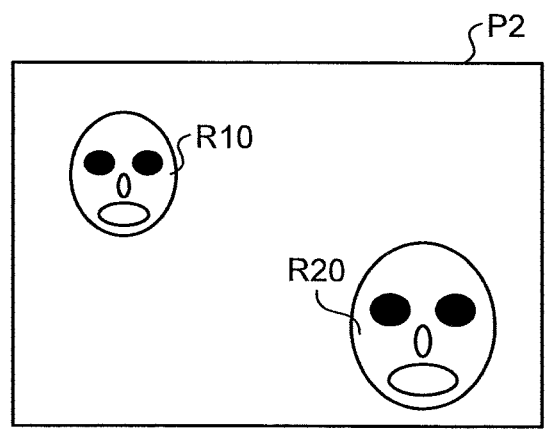
FIG. 14 is a diagram illustrating an example of an image corresponding to RAW image data generated by an imaging unit according to the second embodiment of the present invention.

As illustrated in FIG. 13, first, the face detector 35 detects face areas included in a face of the subject in the RAW image corresponding to the RAW image data acquired by the acquisition unit 31 from the imaging unit 2 by using a technique of well-known pattern matching or the like. More specifically, in the case illustrated in FIG. 14, the face detector 35 detects face areas R10 and R20 (step S501).

Subsequently, the determination unit 32 extracts the pixel values of the pixels corresponding to the narrow band filters C6 of the face areas detected by the face detector 35 (step S502).

After that, the determination unit 32 calculates an average value Ave_C6 of the face areas detected by the face detector 35 (step S503).

Subsequently, the determination unit 32 determines whether or not the average value Ave_C6 of each of the face areas calculated in step S503 is larger than the threshold value Th_ILL (step S504). In a case where the average value Ave_C6 is larger than the threshold value Th_ILL (step S504: Yes), the determination unit 32 determines that sufficient near-infrared information is included in the face areas (step S505). On the contrary, in a case where the average value Ave_C6 of the face areas calculated in step S503 is equal to or smaller than the threshold value Th_ILL (step S504: No), the determination unit 32 determines that sufficient near-infrared information is not included in the face areas (step S506).

After step S505 or step S506, in a case where the determination of the determination unit 32 with respect to all the face areas detected by the face detector 35 is ended (step S507: Yes), the image processing unit 3 returns to the main routine of FIG. 4. On the contrary, in a case where the determination of the determination unit 32 with respect to all the face areas detected by the face detector 35 is not ended (step S507: No), the image processing unit 3 returns to step S504.

According to the second embodiment of the present invention described heretofore, it is possible to obtain the same effects as those of the above-described first embodiment, and since the wide band filters C1 to C3 are omitted, it is possible to embody the present invention at a low cost.

In addition, according to the second embodiment of the present invention, since the filter array 221a are configured with only the narrow band filters C4 to C6, it is possible to generate vital information at a high accuracy.

In addition, in the second embodiment of the present invention, although the determination unit 32 determines whether or not sufficient near-infrared information is included in the face areas detected by the face detector 35, the determination unit may perform the determination of whether or not sufficient near-infrared information is included for every predetermined area of the RAW image, for example, every four-divided area of the RAW image.

Third Embodiment

Next, a third embodiment of the present invention will be described. The configuration of an imaging device according to the third embodiment of the present invention is different from that of the above-described first embodiment. More specifically, although the imaging device according to the first embodiment determines based on the RAW image data generated by the imaging unit 2 whether or not sufficient near-infrared information is included, the imaging device according to the third embodiment further includes a sensor which detect the near-infrared information. Therefore, hereinafter, after the configuration of the imaging device according to the third embodiment is described, processes performed in the third embodiment will be described. In addition, the same components as those of the imaging device 1 according to the first embodiment are denoted by the same reference signs, and the description thereof is omitted.

Configuration of Imaging Device

Figure 15:
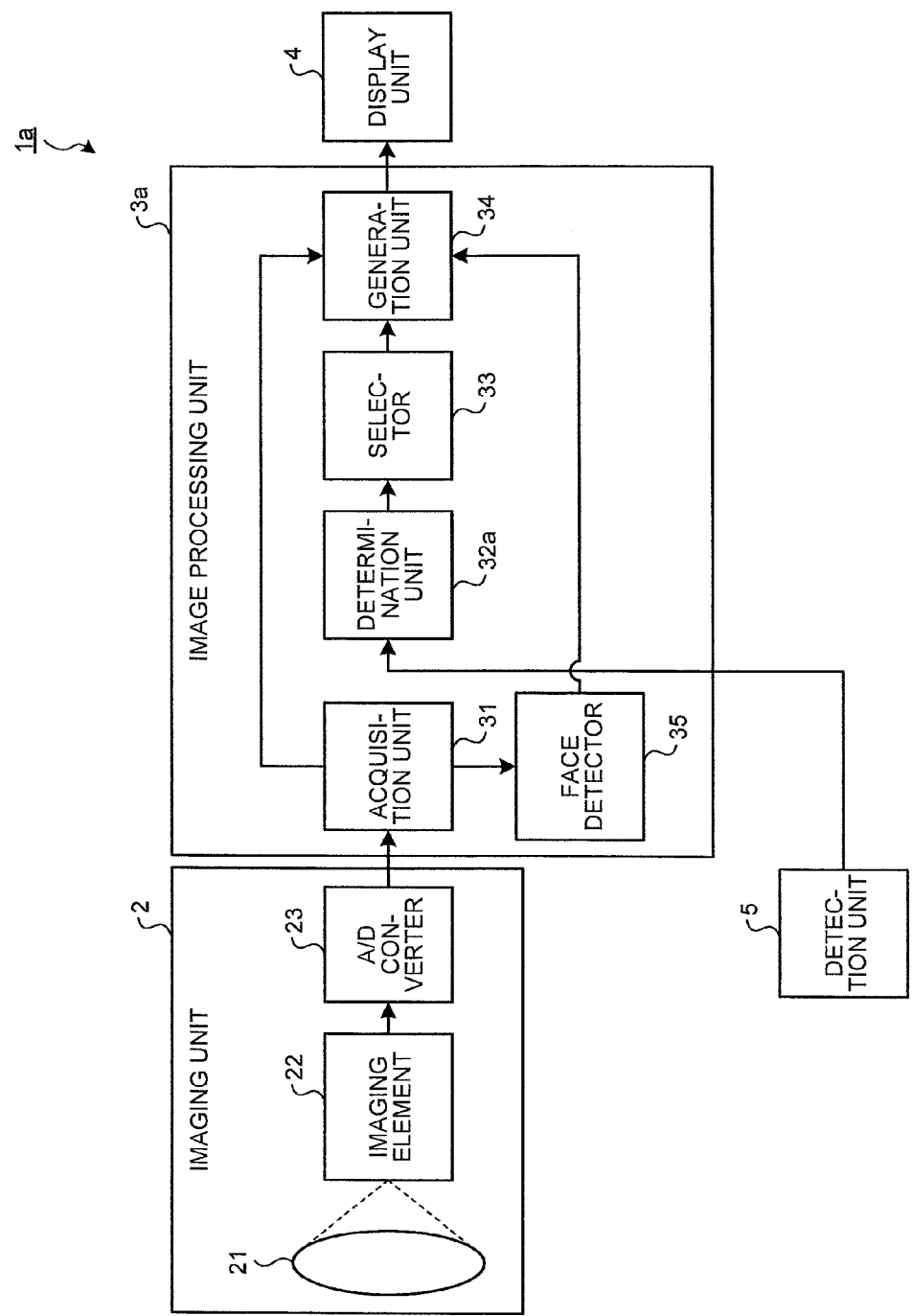
FIG. 15 is a block diagram illustrating a functional configuration of an imaging device according to a third embodiment of the present invention.

FIG. 15 is a block diagram illustrating a functional configuration of the imaging device according to the third embodiment. An imaging device 1a illustrated in FIG. 15 is configured to further include a detection unit 5 in addition to the configuration of the imaging device 1 according to the above-described first embodiment. In addition, the imaging device 1a is configured to include an image processing unit 3a instead of the image processing unit 3 according to the above-described first embodiment.

The detection unit 5 receives light irradiated from the light source to detect an intensity of a predetermined wavelength band and outputs the detection result to a determination unit 32a.

The image processing unit 3a is configured to include the determination unit 32a instead of the determination unit 32 in the image processing unit 3 according to the above-described first embodiment. The determination unit 32a determines whether or not sufficient near-infrared information is included in the RAW image data generated by the imaging unit 2 based on the detection result input from the detection unit 5.

The imaging device 1a having the above configuration executes the same process as those of the above-described first embodiment (refer to FIG. 4).

According to the third embodiment of the present invention described heretofore, since the determination unit 32a determines whether or not sufficient near-infrared information is included in the RAW image data generated by the imaging unit 2 based on the detection result of the detection unit 5, it is possible to determine light source information at a high accuracy.

Fourth Embodiment

Now, a fourth embodiment of the present invention will be described. The configuration of the fourth embodiment is different from that of the above-described third embodiment. More specifically, in the fourth embodiment, the determination unit determines based on the detection result of the detection unit or the RAW image data generated by the imaging unit whether or not sufficient near-infrared information is included. Therefore, hereinafter, the configuration of the fourth embodiment will be described. In addition, the same components as those of the image device 1a according to the third embodiment are denoted by the same reference signs, and the description thereof is omitted.

Figure 16:
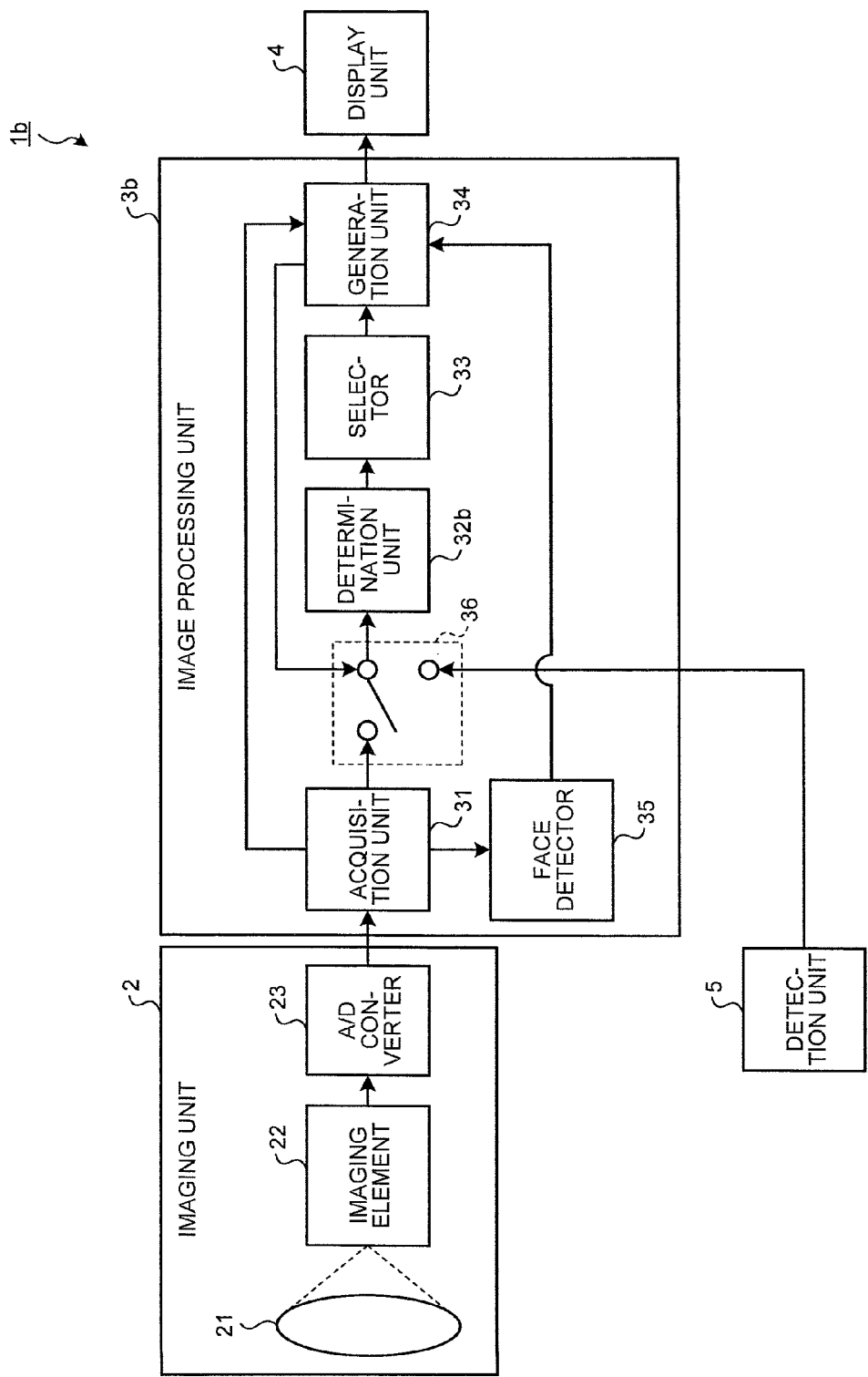
FIG. 16 is a block diagram illustrating a functional configuration of an imaging device according to a fourth embodiment of the present invention.

FIG. 16 is a block diagram illustrating a functional configuration of an imaging device according to the fourth embodiment. An imaging device 1b illustrated in FIG. 16 is configured to include an image processing unit 3b instead of the above-described image processing unit 3a. The image processing unit 3b is configured to further include a switch unit 36 in addition to the configuration of the above-described image processing unit 3a.

The switch unit 36 switches the data which are to be input to a determination unit 32b to any one of the RAW image data acquired by the acquisition unit 31 from the imaging unit 2 and the detection result of the detection unit 5 under the control of the generation unit 34. For example, in a case where the determination unit 32b determines that sufficient near-infrared information is not included in the RAW image data, the switch unit 36 inputs the detection result of the detection unit 5 to the determination unit 32b by driving the switch unit 36.

According to the fourth embodiment of the present invention described heretofore, since the determination unit 32b determines whether or not sufficient near-infrared information is included in the RAW image data generated by the imaging unit 2 based on the detection result of the detection unit 5 or the RAW image data acquired by the acquisition unit 31 from the imaging unit 2, it is possible to determine light source information at a high accuracy.

Other Embodiments

In the above-described first to fourth embodiments, although the generation unit 34 generates the vital information by using any one of the pixel value of the pixel corresponding to the narrow band filter C4 and the pixel value of the pixel according to the narrow band filter C6, for example, in the case of the light source such as a halogen light source being sensitive to the visible light wavelength band and the near-infrared wavelength band, the generation unit may generate the vital information by using the pixel value of the pixel corresponding to the narrow band filter C4 and the pixel value of the pixel according to the narrow band filter C6.

Figure 17:
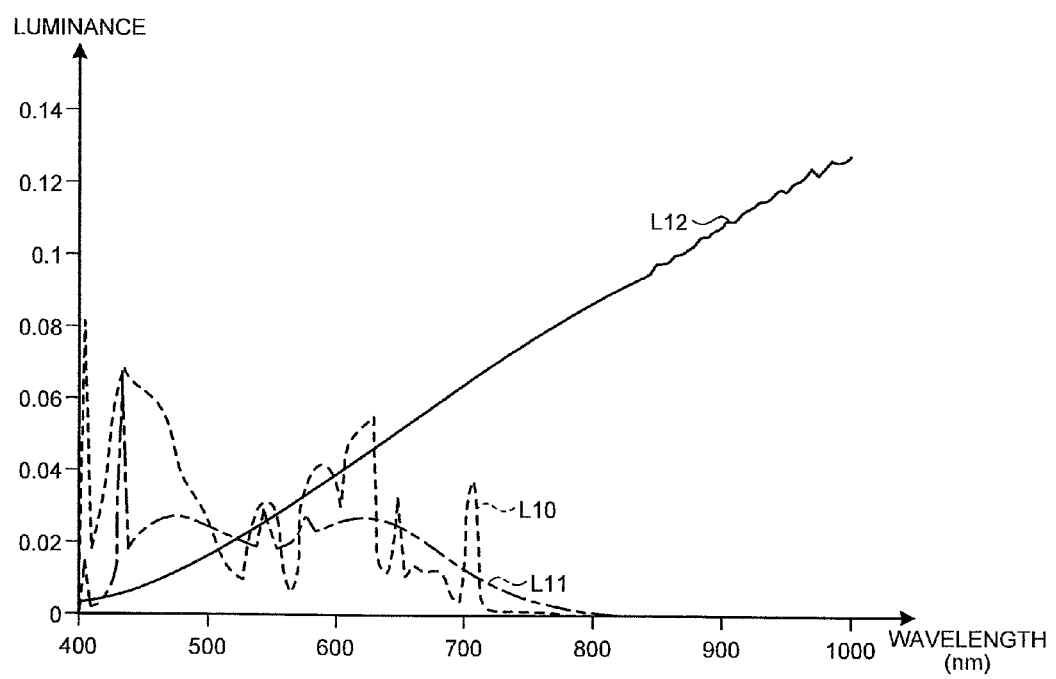
FIG. 17 is a diagram illustrating a relation between a light source spectrum and sensitivity.

FIG. 17 is a diagram illustrating a relation between a light source spectrum and sensitivity. In FIG. 17, the horizontal axis represents wavelength (nm), and the vertical axis represents luminance (W/m$^2$). In addition, in FIG. 17, a curve L10 represents luminance distribution of a fluorescent light lamp (first one thereof), a curve L11 represents luminance distribution of a fluorescent light lamp (second one thereof), and a curve L12 represents luminance distribution of a halogen light source.

As illustrated in the curve L12 of FIG. 17, the halogen light source is sensitive to the visible light wavelength band and the near-infrared wavelength band. Therefore, the generation unit 34 compares the vital information generated by using the pixel value of the pixel corresponding to the narrow band filter C4 and the vital information generated by using the pixel value of the pixel corresponding to the narrow band filter C6 and outputs the vital information having higher reliability to the display unit 4. Herein, the reliability is stability of the vital information among a plurality of frames continuously generated by the imaging unit 2, for example, a rate of change. Therefore, it is possible to further improve the accuracy of the vital information.

In addition, in the present invention, although the generation unit 34 generates the vital information by using the same narrow band filter over the entire image corresponding to the RAW image data, the generation unit may select the to-be-used narrow band filter, for example, for every predetermined area of the image or every face area detected by the face detector 35 and generate the vital information.

The present invention is not limited to the above-described embodiments, but various modifications and applications are available within the scope of the present invention. For example, besides the imaging device used for description of the present invention, the present invention can be applied to any device capable of shooting a subject such as a mobile device or a wearable device having an imaging element of a mobile phone or a smartphone or an imaging device of imaging the subject by using an optical device such as a video camera, an endoscope, a surveillance camera, or a microscope.

In addition, in the specification, in the description of the flowcharts for the operations described above, for the convenience, "first", "next", "subsequently", "after that", and the like are used to description the operations, but these do not denote that the operations are necessarily performed in this order.

In addition, the methods of the processes of the image processing device in the above-described embodiments, that is, all the processes illustrated in the flowcharts may be stored as a program which can be executed by a processor such as a CPU. Besides, the program may be distributed in a form that the program is stored in a recording medium of an external storage device such as a memory card (ROM card, RAM card, or the like), a magnetic disk, an optical disk (CD-ROM, DVD, or the like), or a semiconductor memory. The processor such as a CPU reads the program stored in the recording medium of the external storage device and controls the operations by the read program to execute the above-described processes.

According to some embodiments, it is possible to achieve miniaturization of the device.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
an acquisition unit configured to acquire image data generated by an imaging element where each of narrow band filters constituting a predetermined array pattern is disposed at a position corresponding to any one of a plurality of pixels, the narrow band filters being a first narrow band filter having a wavelength band narrower than a primary-color wavelength band and transmitting narrow band light having a maximum value of transmission spectrum in a visible light range, a second narrow band filter having a wavelength band narrower than the primary-color wavelength band and transmitting narrow band light having a maximum value of transmission spectrum in a visible light range different from that of the first narrow band filter, and a third narrow band filter transmitting narrow band light having a maximum value of transmission spectrum in an invisible light range;
a determination unit configured to determine whether or not a light amount of the invisible light range under an environment at the time when the imaging element generates the image data is larger than a threshold value; and
a generation unit configured to generate vital information of a subject by using a pixel value corresponding to the position of the pixel where the third narrow band filter is disposed and a pixel value corresponding to the position of the pixel where the second narrow band filter is disposed in an image corresponding to the image data in a case where the determination unit determines that the light amount of the invisible light range is larger than the threshold value and to generate vital information of a subject by using a pixel value corresponding to the position of the pixel where the first narrow band filter is disposed and a pixel value corresponding to the position of the pixel where the second narrow band filter is disposed in the image corresponding to the image data in a case where the determination unit determines that the light amount of the invisible light range is equal to or smaller than the threshold value.

2. The image processing device according to claim 1, wherein the determination unit is configured to determine whether or not the light amount of the invisible light range is larger than the threshold value based on the pixel value corresponding to the position in the image where the third narrow band filter is disposed in the image corresponding to the image data.

3. The image processing device according to claim 1, further comprising a detection unit configured to detect light of the invisible light range in the vicinity of the image processing device,
wherein the determination unit is configured to determine whether or not a light amount of the invisible light range is larger than the threshold value based on a detection result detected by the detection unit.

4. The image processing device according to claim 1, wherein the imaging element is configured with a predetermined array pattern including a wide band filter which transmits any one of light of a red wavelength band, light of a green wavelength band, and light of a blue wavelength band, the first narrow band filter, the second narrow band filter, and the third narrow band filter and is configured so that each of the filters constituting the array pattern is disposed at a position corresponding to any one of the plurality of pixels.

5. The image processing device according to claim 1, wherein the determination unit is configured to divide the image corresponding to the image data into a plurality of areas and to determine whether or not the light amount of the invisible light range is larger than the threshold value for respective the areas, and
wherein the generation unit is configured to generate the vital information for respective the areas.

6. The image processing device according to claim 1, wherein the determination unit is configured to determine whether or not the light amount of the invisible light range is larger than the threshold value for a partial area which is a portion of the image corresponding to the image data, and wherein the generation unit is configured to generate the vital information for the partial area.

7. The image processing device according to claim 6, further comprising a face detector configure to detect a face of a subject included in the image corresponding to the image data,
wherein the determination unit is configured to determine whether or not the light amount of the invisible light range is larger than the threshold value for an area including the face detected by the face detector.

8. The image processing device according to claim 1,
wherein the first narrow band filter is configured to transmit narrow band light included in a portion of a green wavelength band,
wherein the second narrow band filter is configured to transmit narrow band light included in a portion of a red wavelength band, and
wherein the third narrow band filter is configured to transmit narrow band light included in a portion of a near-infrared wavelength band.

9. The image processing device according to claim 8,
wherein the first narrow band filter is configured to transmit narrow band light included in a wavelength band of 490 to 550 nm,
wherein the second narrow band filter is configured to transmit narrow band light included in a wavelength band of 620 to 700 nm, and
wherein the third narrow band filter is configured to transmit narrow band light included in a wavelength band of 800 to 1000 nm.

10. The image processing device according to claim 1, wherein the vital information is any one of a degree of oxygen saturation, a heart rate, and a blood pressure.

11. An imaging device comprising:
the image processing device according to claim 1; and
the imaging element.

12. An image processing method executed by an image processing device, comprising:
an acquisition step of acquiring image data generated by an imaging element where each of narrow band filters constituting a predetermined array pattern is disposed at a position corresponding to any one of a plurality of pixels, the narrow band filters being a first narrow band filter having a wavelength band narrower than a primary-color wavelength band and transmitting narrow band light having a maximum value of transmission spectrum in a visible light range, a second narrow band filter having a wavelength band narrower than the primary-color wavelength band and transmitting narrow band light having a maximum value of transmission spectrum in a visible light range different from that of the first narrow band filter, and a third narrow band filter transmitting narrow band light having a maximum value of transmission spectrum in an invisible light range;
a determination step of determining whether or not a light amount of the invisible light range under an environment at the time when the imaging element generates the image data is larger than a threshold value; and
a generation step of generating vital information of a subject by using a pixel value corresponding to the position of the pixel where the third narrow band filter is disposed and a pixel value corresponding to the position of the pixel where the second narrow band filter is disposed in an image corresponding to the image data in a case where it is determined in the determination step that the light amount of the invisible light range is larger than the threshold value and generating the vital information of the subject by using a pixel value corresponding to the position of the pixel where the first narrow band filter is disposed and a pixel value corresponding to the position of the pixel where the second narrow band filter is disposed in the image corresponding to the image data in a case where it is determined in the determination step that the light amount of the invisible light range is equal to or smaller than the threshold value.

13. A non-transitory computer-readable recording medium recording a program for causing an image processing device to execute:
an acquisition step of acquiring image data generated by an imaging element where each of narrow band filters constituting a predetermined array pattern is disposed at a position corresponding to any one of a plurality of pixels, the narrow band filters being a first narrow band filter having a wavelength band narrower than a primary-color wavelength band and transmitting narrow band light having a maximum value of transmission spectrum in a visible light range, a second narrow band filter having a wavelength band narrower than the primary-color wavelength band and transmitting narrow band light having a maximum value of transmission spectrum in a visible light range different from that of the first narrow band filter, and a third narrow band filter transmitting narrow band light having a maximum value of transmission spectrum in an invisible light range;
a determination step of determining whether or not a light amount of the invisible light range under an environment at the time when the imaging element generates the image data is larger than a threshold value; and
a generation step of generating vital information of a subject by using a pixel value corresponding to the position of the pixel where the third narrow band filter is disposed and a pixel value corresponding to the position of the pixel where the second narrow band filter is disposed in an image corresponding to the image data in a case where it is determined in the determination step that the light amount of the invisible light range is larger than the threshold value and generating the vital information of the subject by using a pixel value corresponding to the position of the pixel where the first narrow band filter is disposed and a pixel value corresponding to the position of the pixel where the second narrow band filter is disposed in the image corresponding to the image data in a case where it is determined in the determination step that the light amount of the invisible light range is equal to or smaller than the threshold value.

* * * * *